(12) United States Patent
Francke et al.

(10) Patent No.: US 6,600,804 B2
(45) Date of Patent: *Jul. 29, 2003

(54) GASEOUS-BASED RADIATION DETECTOR AND APPARATUS FOR RADIOGRAPHY

(75) Inventors: Tom Francke, Sollentuna (SE); Juha Rantanen, Solna (SE); Christer Ullberg, Sollentuna (SE)

(73) Assignee: XCounter AB, Danderyd (SE)

( * ) Notice: Subject to any disclaimer, the term of this patent is extended or adjusted under 35 U.S.C. 154(b) by 179 days.

This patent is subject to a terminal disclaimer.

(21) Appl. No.: 09/760,748

(22) Filed: Jan. 17, 2001

(65) Prior Publication Data

US 2002/0003860 A1 Jan. 10, 2002

Related U.S. Application Data

(63) Continuation-in-part of application No. 09/443,320, filed on Nov. 19, 1999.

(30) Foreign Application Priority Data

Oct. 13, 2000 (SE) .................................................. 0003718

(51) Int. Cl.[7] .................................................. G01N 23/06
(52) U.S. Cl. ........................................ 378/51; 250/374
(58) Field of Search ............................. 378/51, 370.13, 378/98.8; 250/374, 385.1

(56) References Cited

U.S. PATENT DOCUMENTS

| 4,629,897 | A | * | 12/1986 | Lemonnier et al. | .......... 250/385 |
| 4,642,465 | A | | 2/1987 | Britten | |
| 5,308,987 | A | | 5/1994 | Wuest et al. | |
| 5,596,201 | A | | 1/1997 | Charpak | |
| 5,604,783 | A | | 2/1997 | Charpak | |
| 5,731,584 | A | | 3/1998 | Beyne et al. | |
| 6,011,265 | A | * | 1/2000 | Sauli | ........................ 250/374 |
| 6,046,454 | A | | 4/2000 | Lingren et al. | |
| 6,069,362 | A | | 5/2000 | Giakos | |
| 6,385,282 | B1 | * | 5/2002 | Francke et al. | ............. 250/374 |

FOREIGN PATENT DOCUMENTS

| EP | 0810631 | 3/1997 |
| FR | 2 790 100 | 8/2000 |
| WO | 9923859 | 5/1999 |
| WO | WO 00/49639 | 8/2000 |

* cited by examiner

Primary Examiner—Robert H. Kim
Assistant Examiner—Irakli Kiknadze
(74) Attorney, Agent, or Firm—Birch, Stewart, Kolasch & Birch, LLP

(57) ABSTRACT

A detector for detection of ionizing radiation comprises a cathode; an anode; an ionizable gas arranged between these electrodes; a radiation entrance arranged such that ionizing radiation can enter and ionize the ionizable gas; and a readout arrangement. A voltage across the electrodes causes electrons created during ionization of the gas to drift towards the anode, where the readout arrangement detects them. To reduce the risk of occurrence of sparks, and/or to reduce the energy in occurring sparks, one of the cathode and anode has at least the surface layer facing the other electrode made of a material having a resistivity of at least $5 \times 10^{-8}$ $\Omega$m.

60 Claims, 4 Drawing Sheets

GASEOUS-BASED RADIATION DETECTOR AND APPARATUS FOR RADIOGRAPHY

This application is a continuation-in-part of application Ser. No. 09/443,320 filed on Nov. 19, 1999.

FIELD OF THE INVENTION

The invention relates to gaseous-based detectors for detection of ionizing radiation and to apparatus for radiography.

BACKGROUND OF THE INVENTION AND RELATED ART

Gaseous-based ionizing radiation detectors, in general, are very attractive since they are cheap to manufacture, and since they can employ gas multiplication to strongly amplify the signal amplitudes.

A typical gaseous-based ionizing radiation detector comprises a planar cathode and anode arrangement, respectively, and an ionizable gas arranged between the cathode and anode arrangements. The detector is arranged such that a radiation beam from a radiation source can enter the detector for ionizing the ionizable gas. Further, a voltage is typically applied for drifting electrons created during ionization of the ionizable gas towards the anode. The voltage and the design of the detector electrodes may be adjusted such that multiplication of electrons is achieved to induce an amplified charge at the anode arrangement. A readout arrangement, which typically includes a plurality of readout elements, is arranged adjacent the anode arrangement for detecting the electrons drifted towards the anode arrangement.

A particular kind of gaseous detector is the one, in which electrons released by interactions between photons and gas atoms can be extracted in a direction essentially perpendicular to the incident radiation. Hereby, an improved spatial resolution is obtained.

However, in all kind of gaseous-based ionizing radiation detectors spark discharges can occur in the gas due to the strong electric fields created in the detector. Such events are particularly probable to occur in high amplification detectors.

The spark discharges block the detector for a period of time, and can also be harmful for the detector and particularly for electronics thereof.

SUMMARY OF THE INVENTION

A main object of the invention is to provide a detector for detection of ionizing radiation wherein problems caused by spark discharges are eliminated, or at least reduced.

In this respect a particular object of the invention is to provide such detector wherein the energy in any occurring sparks is low such that relatively few charges are released in the gas.

A further object of the present invention is to provide such detector, which provides for fast recovery subsequent to a spark discharge, and thus provides for faster detection and shorter time periods during which an object under investigation is exposed for ionizing radiation.

Yet a further object of the invention is to provide such detector, which is effective, accurate, and of low cost.

Still a further object of the invention is to provide such detector, which is reliable and has a long lifetime.

In this respect there is a particular object of the invention to provide such detector, which protects the anode and readout electronics such as e.g. preamplifiers from being damaged by high energy sparks.

Yet a further object of the invention is to provide an apparatus for planar beam radiography, comprising a detector for detection of ionizing radiation, which limits the problems caused by spark discharges.

Such objects, among others, are attained by radiation detectors and apparatus for planar beam radiography as claimed in the appended claims.

Further characteristics of the invention and advantages thereof will be evident from the following detailed description of preferred embodiments of the invention, which are also illustrated in the accompanying drawings.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF PREFERRED EMBODIMENTS

Figure 1:
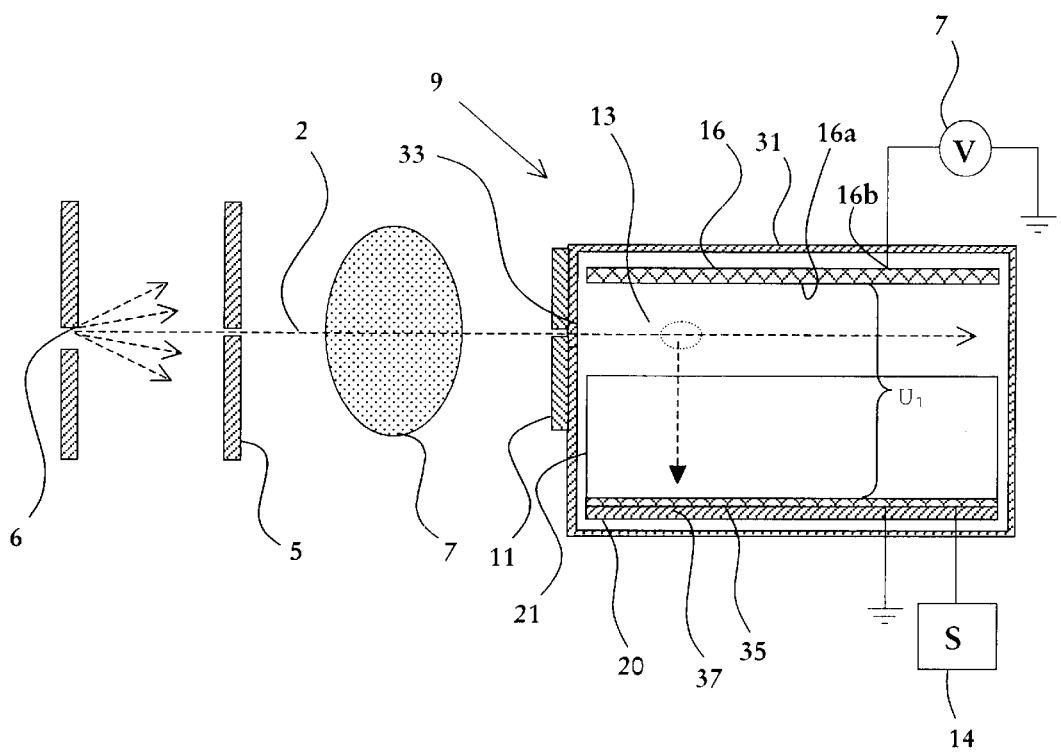
FIG. 1 illustrates schematically, in an overall view, an apparatus for planar beam radiography, according to a first embodiment of the present invention.

FIG. 1 is a sectional view in a plane orthogonal to the plane of a planar fan-shaped X-ray beam 2 of a device for planar beam radiography, according to a first embodiment of the present invention. The device includes an X-ray source 6, which together with a first thin collimator window 5 produces the planar X-ray beam 2, for irradiation of an object 7 to be imaged.

The beam transmitted through the object 7 enters a detector 9. Optionally a thin slit or second collimator window 11, which is aligned with the X-ray beam, forms the entrance for the X-ray beam 2 to the detector 9.

The detector 9 is oriented such that the X-ray photons can enter sideways between a cathode arrangement 16 and an anode arrangement 20 between which a space 13 capable of being filled with an ionizable gas or gas mixture is arranged. By means of a high voltage DC supply unit 7 a voltage $U_1$ can be applied between cathode 16 and anode 20 for drift of electrons and ions in space 13. Cathode 16 and anode 20 arrangements are preferably substantially parallel with each other.

X-ray source 6, thin collimator window 5, optional collimator window 11 and detector 9 are preferably connected and fixed in relation to each other by a suitable means for example a frame or support (not shown in FIG. 1).

The ionizable gas or gas mixture comprising for example 90% krypton and 10% carbon dioxide or for example 80% xenon and 20% carbon dioxide. The gas may be under pressure, preferably in a range 1–20 atm. Therefore, the detector includes a gas tight housing 31 with a slit entrance window 33, through which the X-ray beam 2 can enter the detector. In FIG. 1 the casing 31 encloses major parts of detector 9. It shall, however, be appreciated that casing 31 may be arranged in other manners as long as the space between the electrodes may be enclosed.

Furthermore, detector 9 comprises a readout arrangement for separate detection of the electrons drifted towards anode arrangement 20 and/or ions drifted towards the cathode arrangement 16. The readout arrangement may be comprised of anode arrangement 20 itself as illustrated in FIG. 1, or a separate readout arrangement may be arranged adjacent anode arrangement 20 adjacent cathode arrangement 16, or elsewhere.

Anode or readout arrangement 20 comprises an array of conductive elements or strips 35 arranged side by side and electrically insulated from each other on a dielectric layer or substrate 37. The strips 35 may be formed by photolithographic methods or electroforming, etc.

To provide for an increased spatial resolution and for compensation for parallax errors in any detected images strips 35 extend essentially in directions parallel to the direction of incident X-ray photons of beam 2, originating from source 6, at each location. Thus, given a divergent beam 2, readout strips 35 are arranged in a fan-like configuration. The length and width of strips 35 are adjusted to the specific detector in order to obtain the desired (optimal) spatial resolution and sensitivity.

Each of the strips 35 is preferably connected to readout and signal processing electronics 14 by means of a respective separate signal conductor (of which only one is illustrated in FIG. 1), whereby the signals from each strip can be processed separately. As the readout strips 35 also constitute the anode, the signal conductors also connect the respective strip to the high voltage DC power supply unit 7, with suitable couplings for separation. In FIG. 1 such provisions are merely indicated by a separate ground connector.

The above-depicted design of the readout arrangement provides for capability of separate detection of electrons derivable mainly from ionization by transversely separated portions of planar radiation beam 2 by strips 35. In such manner one-dimensional imaging is enabled.

In the case the readout arrangement is a separate arrangement, anode strips 35 can be formed as a unitary electrode without strips.

In an alternative configuration of anodes/readout arrangement (not illustrated), the strips are further divided into segments in the direction of the incident X-rays, the segments being electrically insulated from each other. Preferably a small spacing extending perpendicular to the incident X-rays is provided between each segment of respective strip. Each segment is connected to the processing electronics by means of a separate signal conductor, where the signals from each segment preferably are processed separately. Such readout arrangement can be used when energy-resolved detection of radiation is required. In this respect specific reference is made to our co-pending Swedish patent application Swedish patent application No. 0001167-6 entitled Spectrally resolved detection of ionizing radiation and filed on Mar. 31, 2000, which application hereby is incorporated by reference.

Furthermore, detector 9 comprises an electron avalanche amplification device 21 for avalanche amplification of electrons drifted within space 13. To such end electron avalanche amplification device 21 is suitably connected to high voltage DC supply unit 7. In one version the electron avalanche amplification device 21 is comprised of a grid-like conductive sheet or similar, which defines a plurality of holes, through which electrons may pass on their way towards the anode arrangement 20.

In operation, the incident X-rays 2 enter the detector through the optional thin slit or collimator window 11, if present, and between cathode 16 and anode 20, preferably in a center plane between them as indicated in FIG. 1. The incident X-rays 2 then travel through the gas volume in a direction preferably substantially parallel with electrodes 16 and 20 and get absorbed, thus ionizing gas molecules in space 13. Each X-ray photon produces a primary ionization electron-ion pair within the gas as a result of interaction with a gas atom. This production is caused by photo effect, Compton effect or Auger-effect. Each primary electron produced looses its kinetic energy through interactions with new gas molecules, causing further production of electron-ion pairs (secondary ionization electron-ion pairs). Typically between a few hundred and thousand secondary ionization electron-ion pairs are produced from a 20 keV X-ray photon in this process.

The freed electrons in space 13 will drift towards anode arrangement 20 due to the voltage $U_1$ applied. If the voltages are kept high enough and if field concentration means are provided (as discussed above) the freed electrons are avalanche amplified during their travel towards the anode. If an electron avalanche amplification device is provided it is preferably held at electrical potential(s) such that a weak drift field is obtained between the cathode arrangement 16 and the amplification device 21 and strong avalanche amplification field is obtained within amplification device (e.g. between an electrode thereof and anode arrangement 20).

The moving electrons induce charges in the strips 35 of the anode/readout arrangement 20 which are detected. If no avalanche amplification takes place the major part of the signal is due to collection of the liberated charges.

Each incident X-ray photon causes generally one induced pulse in one (or more) anode strip. The pulses are processed in the rad-out and signal processing electronics 14, which eventually shapes the pulses, and integrates or counts the pulses from each strip representing one picture element. The signals are further amplified and processed by readout circuitry 14 to obtain accurate measurements of the X-ray photon interaction points, and optionally the X-ray photon energies.

Due to the high electric field strengths that can occur in connection with the electrode plates there is a risk that spark discharges occur in the gas. Such spark discharges blocks the detector for a period of time, and can also damage the anode arrangement 20 and electronics connected thereto.

In order to reduce the risk that spark discharges occur in the gas and to reduce the energy released by spark discharges that nevertheless do occur the present invention involves providing the cathode arrangement 16 (and/or the anode strips 35) of a material having a resistivity of at least $5\times10^{-8}$ $\Omega$m.

The cathode arrangement 16 is preferably of a material having a resistivity between $5\times10^{-8}$ $\Omega$m and $1\times10^{5}$ $\Omega$m, more preferably between $1\times10^{-3}$ Ωm and $1\times10^{3}$ Ωm, even more preferably between $1\times10^{-2}$ Ωm and 1 Ωm, and most preferably between $1\times10^{-2}$ Ωm and $1\times10^{-1}$ Ωm. The material can be a doped or undoped semiconducting material preferably comprising a semiconductor material composed of elements selected from the periodic system groups IV (e.g. the compounds silicon and germanium) and III–V (e.g. the compounds GaAs, InP, and InGaAsP). Preferably though, the cathode arrangement 16 is of undoped or doped silicon. Alternatively, the material is an electrically conducting glass, a plastic material, diamond or silicon monoxide. In fact, virtually any solid material having a resistivity in the ranges mentioned above may be suitable to employ in the cathode arrangement 16.

By such provisions the resistive cathode arrangement 16 faces space 13 and avalanche amplification means 21, where strong electric fields can occur. Hereby, in case a spark discharge is to occur, electrons within a much smaller area will participate and become released from the cathode surface in the spark, and thus the energy of the spark discharge is small. Thus the effects due to the same can be controlled.

Nevertheless, such resistances limit the rate of X-ray photons that can be detected without significant decrease of the electrical field strength in the detector. Obviously, one has to find a suitable optimum between the rate and the risk of occurrence of spark discharges (and their respective energies).

As an alternative to provide the cathode arrangement 16 entirely made of such semiconducting material only the surface layer 16a of cathode arrangement 16 facing space 13 may be made of a material having a resistivity of at least $5\times10^{-8}$ Ωm. In such instance the surface layer may be provided on a conductive substrate or on a dielectric substrate provided with suitable electric connections (not illustrated).

Figure 2:
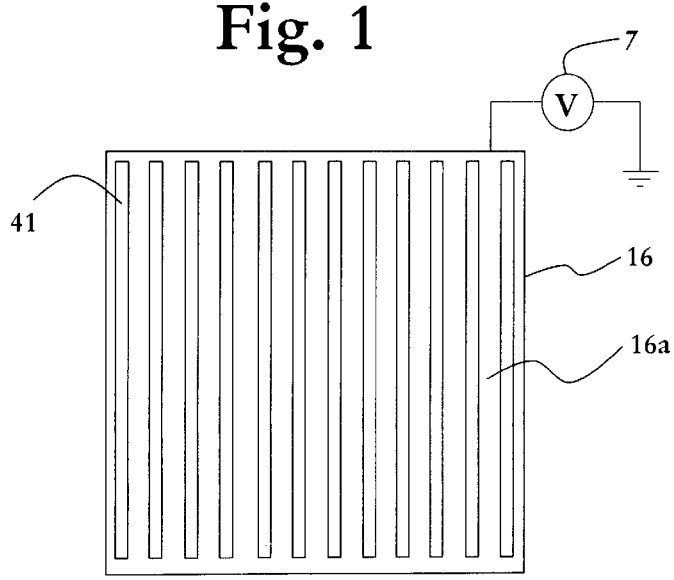
FIG. 2 is a schematic plane view of a cathode arrangement of a detector according to a second embodiment of the present invention.

As yet an alternative the surface layer 16a of cathode arrangement 16 facing space 13 may be partly covered by a plurality of electrically conductive elements electrically connected to each other only by means of said resistive material. Such a cathode arrangement is illustrated in FIG. 2 wherein one of said plurality of electrically conductive elements is denoted by reference numeral 41. By such provisions a faster detector may be provided, wherein the surface area of high conductivity is still limited to local areas (i.e. the respective elements 41). Although, elements 41 of FIG. 2 are illustrated as elongated stripes they may have other shapes and be arranged in other patterns. For example, the electrically conductive elements may be quadratic or rectangular pads arranged in a two-dimensional matrix on the surface 16a of the resistive cathode 16.

The high voltage DC supply unit 7 is preferably connected to the backside of cathode 16 as indicated at 16b in FIG. 1 (i.e. at the surface opposite to surface 16a) such that the respective electrically conductive elements 41 are each connected to high voltage DC supply unit 7 via the resistive cathode 16.

Further, in the case the cathode of FIG. 2 is used together with elongated anode/readout strips as described above the elements 41 shall preferably be oriented with respect to the readout strips 35 such that an electric field is obtained within the detector that reduces the occurrence of "pockets" within space 13 and amplification device 21, i.e. regions where electrons and/or ions are not drifted further and will thus be accumulated. This is particularly important to avoid close to the anode/readout arrangement 20. Thus, the plurality of electrically conductive elements 41 of the cathode 16 are oriented substantially in a first direction, and the plurality of electrically conductive or semiconducting elements 35 of the anode/readout arrangement 20 are oriented substantially in a second direction, wherein the first and second directions are essentially non-parallel, and conveniently essentially perpendicular.

Figure 3:
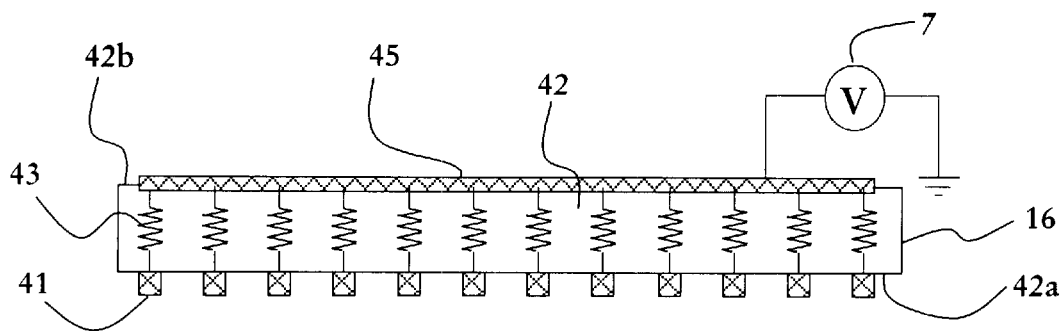
FIG. 3 is an enlarged schematic cross sectional view of a cathode arrangement of a detector according to a third embodiment of the present invention.

In yet a further embodiment of cathode 16, as being illustrated in FIG. 3, such plurality of electrically conductive elements 41 are provided on a surface 42a of a dielectric substrate 42. The cathode arrangement is oriented such that electrically conductive elements 41 and surface 42a of dielectric substrate 42 are facing space 13 and anode 20 of the detector 9. Each of said plurality of elements 43 is connected to an electrically conductive layer 45 arranged on surface 42b of dielectric substrate 42 opposite to surface 42a by means of a respective resistance 43.

In FIG. 3 these resistance are merely symbolically indicated and it shall be appreciated that they may be implemented in a variety of manners; e.g. as discrete components within or adjacent substrate 42 or as integrated components within substrate 42. In the latter instance the complete cathode may be fabricated in a semiconductor process with the resistances implemented as suitably composed layers between a layer of conductive elements 41 and a conductive layer 45 for connection to high voltage DC supply unit 7. Alternatively, the resistances are so-called thick film resistors, which are printed on the substrate and interconnected accordingly.

Figure 4:
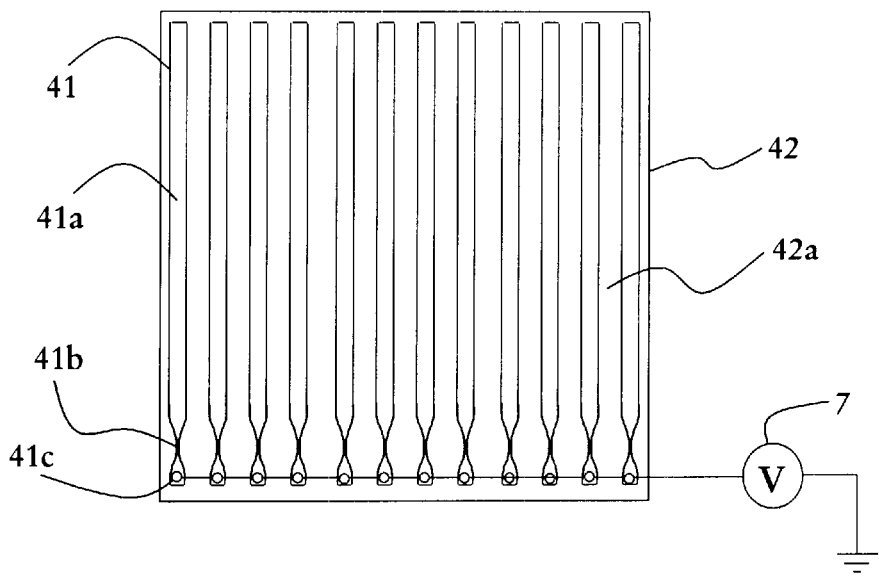
FIG. 4 is a schematic plane view of a cathode arrangement of a detector according to a fourth embodiment of the present invention.

A further alternative of the implementation of the ideas behind the FIG. 3 embodiment is illustrated in FIG. 4. Here, each of the plurality of electrically conductive elements and each of the plurality of resistances are provided on surface 42a of dielectric substrate 42 in the form of a stripe 41 having a narrow waist 41b in an end portion thereof, such that the stripe has an elongated portion 41a constituting the electrically conductive element, a narrow waist portion 41b constituting the resistance, and a wider connection portion 41c for connection to high voltage DC supply unit 7.

Preferably, the material composition of each of stripes 41 is inhomogeneous such that each elongated portion 41a has a material composition of a resistivity, which is lower, particularly considerably lower, than the resistivity of the material composition of each narrow waist portion 41b. Such design may be achieved by firstly depositing a poor conductor such as chromium to define the entire stripes 41a–c, whereafter a good conductor such as gold is deposited on top of said chromium only at the elongated portions 41a, and possibly also at the connection portions 41c.

As an alternative, the narrow waists 41b may be replaced by resistances of the kind described with reference to FIG. 3, but which are disposed on the same side of the substrate 42 as the stripes 41.

Further, while the FIG. 1 embodiment includes particular illustrated avalanche amplification (or field concentration) and readout arrangements, other avalanche amplification and readout arrangements may equally well be utilized in connection with the present invention, such that electrons freed in space 13 and can be amplified and subsequently detected without encountering problems due to spark discharges. Various such avalanche amplification arrangements are described in our co-pending Swedish patent application No. 9901325-2 entitled Radiation detector, an apparatus for use in planar radiography and a method for detecting ionizing radiation and filed on Apr. 14, 1999, which application hereby is incorporated by reference.

In the following a few avalanche amplification and readout arrangement geometries are described.

Figure 5:
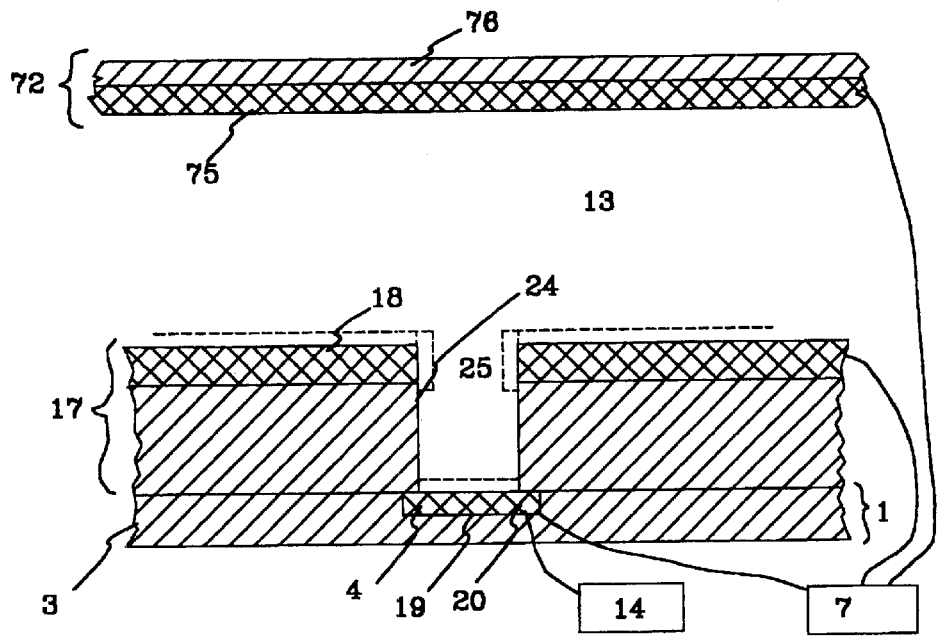
FIG. 5 illustrates schematically, in cross sectional view, a portion of a detector arrangement according to a fifth embodiment of the present invention.

FIG. 5 shows schematically a portion of a cross sectional view of a detector according to a fifth embodiment of the invention. The detector comprising a cathode electrode 72 including a resistive or semiconducting substrate 75 and a conductive layer 76 and an anode 1 including a dielectric substrate 3 and a conductive layer 4 being an anode electrode. Between the electrodes a space 13 filled with an ionizable gas and an electron avalanche amplification arrangement 17 is arranged, the amplification arrangement 17 including an avalanche amplification cathode 18 and an avalanche amplification anode 19, separated by a dielectric 24. (Here, the anode 4 and the avalanche amplification anode 19 are the very same piece of element.) The dielectric 24 could be a gas or a solid substrate 24 carrying the cathode 18 and the anode 19, as shown in FIG. 5. Both, or one, of the cathode 18 and the anode 19 can be provided with a resistive or semiconducting layer on top of a conductive layer so that a surface of the resistive or semiconducting layer is in contact with the gas (shown with broken lines). Alternatively only one of the cathodes 72, 18 or anode 4/19 is provided with a resistive or semiconducting layer, preferably only the anode 4/19. Between the cathode 18 and the anode 4/19 a voltage is applied by means of a DC power supply 7 for creation of a very strong electric field in an avalanche amplification region 25. The avalanche region 25 is formed in a region between and around the edges of the avalanche cathode 18 which are facing each other, where a concentrated electric field will occur due to the applied voltages. The DC power supply 7 is also connected to cathode 72. The voltages applied are selected such that a weaker electric field, drift field, is created over the space 13. Electrons (primary and secondary electrons) released by interaction in space 13 (with incident ionizing radiation, which preferably travels parallel with the electrodes and orthogonally to the plane of the FIG. 5 cross section), being a conversion and drift volume, will drift towards the amplification device 17 due to the drift field. They will enter the very strong avalanche amplification fields and be accelerated. The accelerated electrons will interact with other gas atoms in region 25 causing further electron-ion pairs to be produced. Those produced electrons will also be accelerated in the field, and will interact with new gas atoms, causing further electron-ion pairs to be produced. This process continues during the travel of the electrons in the avalanche region towards anode 19 and an electron avalanche is formed. After leaving the avalanche region the electrons will drift towards anode 19. Possibly the electron avalanche continues up to anode 19 if the electric field is strong enough.

It shall be appreciated that a plurality of anodes 4/19, and regions 25 are provided separate from each other. Each avalanche region 25 is formed by an opening or channel in the cathode 18 and the dielectric substrate 24, if present. The openings or channels can be circular, seen from above, or continuous, longitudinal extending between two edges of the substrate 24, if present, and cathode 18. In the case the openings or channels are circular when seen from above they are arranged in rows, each row of openings or channels including a plurality of circular openings or channels. A plurality of longitudinal openings or channels or rows of circular channels are formed beside each other, parallel with each other or with the incident radiation. Alternatively, the circular openings or channels can be arranged in other patterns.

The anode electrodes 4/19 also forms readout elements 20 in the form of strips provided in connection with the openings or channels forming avalanche regions 25. Preferably, one strip is arranged for each opening or channel or row of openings or channels. The strips could be divided into sections along its length, where one section could be provided for each circular opening or channel or for a plurality of openings or channels, in the form of pads. The strips and the sections, if present, are electrically insulated from each other. Each detector electrode element i.e. strip or section is preferably separately connected to processing electronics 14. Alternatively the readout elements can be located on the backside of the substrate (opposite to the side of the anode electrodes 4/19). In this case it is necessary that the anode electrodes 4/19 are semi-transparent to induced pulses, e.g. in the form of strips or pads.

As an example the longitudinal channels can have a width in the range 0.01–1 mm, the circular channels can have a diameter of the circle being in the range 0.01–1 mm, and the thickness of the dielectric 24 (separation between the avalanche cathode 18 and anode 19) is in the range 0.01–1 mm.

Figure 6:
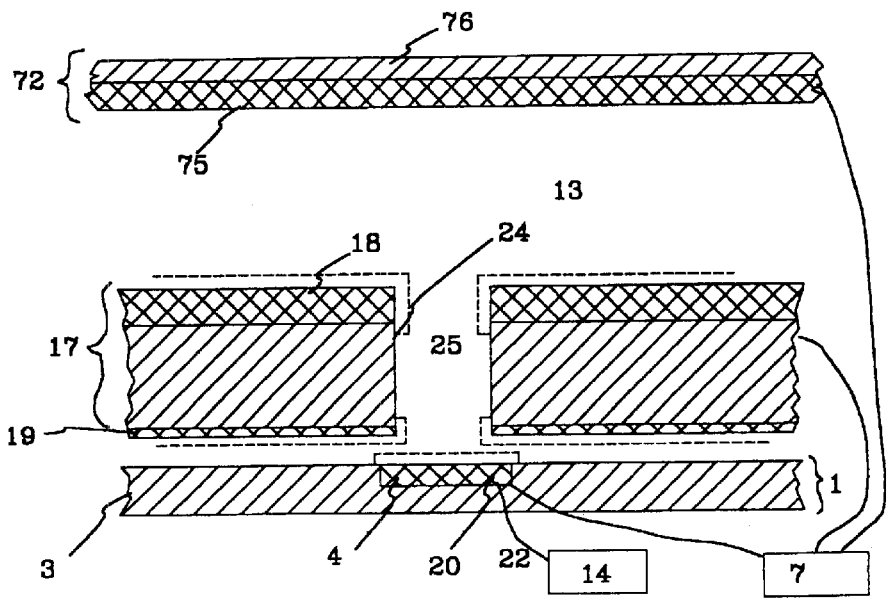
FIG. 6 illustrates schematically, in cross sectional view, a portion of a detector arrangement according to a sixth embodiment of the present invention.

FIG. 6 shows schematically a portion of a cross sectional view of a detector according to a sixth embodiment of the invention. This embodiment differs from the embodiment according to FIG. 5 in that the anode electrodes 4/19 are formed by different conductive elements, being spaced by a dielectric, which could be solid or a gas, and that the openings or channels also are formed in the avalanche anode electrode 19. The avalanche amplification anode 19 is connected to the DC power supply 7. In the case the dielectric between the anode electrodes 4 and 19 is solid, it includes openings or channels through the dielectric, the openings or channels essentially corresponding the openings or channels forming the avalanche regions 25. An electric field is created between the anode electrodes 4 and 19. This field could be a drift field, i.e. a weaker field, or an avalanche amplification field, i.e. a very strong electric field.

Any or all of the cathode 72, 18 and the anode 4, 19 electrodes can be provided with a resistive or semiconducting layer on top of a conductive layer so that a surface of the resistive or semiconducting layer is in contact with the gas (shown with broken lines). Alternatively only one of the cathodes 72, 18 or anodes 4, 19 is provided with a resistive or semiconducting layer, preferably the anode 4.

Figure 7:
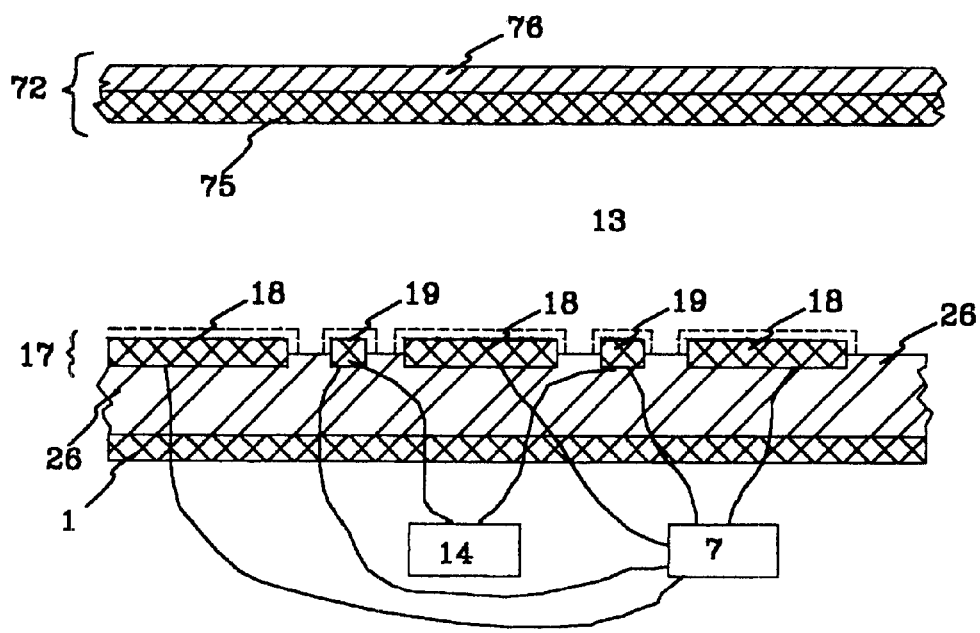
FIG. 7 illustrates schematically, in cross sectional view, a portion of a detector arrangement according to a seventh embodiment of the present invention.

FIG. 7 shows schematically a portion of a cross sectional view of a detector according to a seventh embodiment of the invention. The detector includes a cathode 72, an anode 1, and an avalanche amplification device 17. A space 13 being a conversion and drift volume is provided between the cathode 72 and the avalanche amplification device 17. The gap 13 is gas filled and the cathode 72 is formed as described above. The anode 1 is provided on a back surface of a dielectric substrate 26, e.g. a glass substrate. On the front surface of the substrate 26, avalanche amplification cathode 18 and anode 19 strips are alternately provided. The cathode 18 and anode 19 strips are conductive strips, and are connected to the DC power supply 7, for creation of a concentrated electric field, i.e. an avalanche amplification field in each region between a cathode strip 18 and an anode 19 strip. The anode 1 and cathode 72 are also connected to the DC power supply 7. The voltages applied are selected so that a weaker electric field, drift field, is created over the gap 13. Alternatively the dielectric substrate 26 can be replaced by a gas. The anodes and the cathodes are then supported, e.g. in their respective ends.

Preferably, the avalanche anode strips 19 also form readout elements 20, and are then connected to the processing electronics 14. The avalanche cathode strips 18 could instead form the readout elements, or together with the anode strips 19. As an alternative the anode electrode 1 can be constituted of strips, which can be segmented, and being insulated from each other. Those strips could then form the readout elements alone or together with the anode and/or cathode strips. The strips acting as anode/cathode and readout element are connected to the DC power supply 7 and the processing electronics 14, with appropriate couplings for separation.

Any one of the set of cathode strips 18 and the set of anode strips 19 can be provided with a resistive or semiconducting layer on top of a conductive layer so that a surface of the resistive or semiconducting layer is in contact with the gas. Alternatively only one of the cathode 72, the set of cathode strips 18 and the set of anode strips 19 is provided with a resistive or semiconducting layer. In a further alternative of an arrangement of readout strips the readout strips 20 are arranged under and parallel with the avalanche anode strips 19. The readout strips 20 are then made a little wider than the avalanche anode strips 19. If they are located under the anode 1 it is necessary that the anode electrode is semi-transparent to induced pulses, e.g. in the form of strips or pads. In yet another alternative the anode 1 can be omitted since the necessary electric fields can be created by means of the cathode electrodes 5, 18 and the anode electrodes 19.

As an example, the glass substrate is about 0.1–5 mm thick. Further, the conductive cathode strip has a width being about 20–1000 $\mu$m and the conductive anode strip has a width being about 10–200 $\mu$m, with a pitch of about 50–2000 $\mu$m. Cathodes and anodes can be divided into segments along their extension.

In operation, radiation, e.g. X-ray, photons enter the space 13 in the detector of FIG. 7 essentially parallel with the avalanche cathode 18 and anode 19 strips and perpendicular to the plane of the illustrated cross section. In the conversion and drift volume 13 the incident X-ray photons are absorbed and electron-ion pairs are produced as described above. A cloud of primary and secondary electrons, being the result of interactions caused by one X-ray photon drift towards the avalanche amplification device 17. The electrons will enter the very strong electric field in the gas filled region between an anode strip and a cathode strip, which is an avalanche amplification region. In the strong electric field the electrons initiate electron avalanches. As a result the number of electrons which is collected on the anode strips is of a few orders of magnitude higher than the number of primary and secondary electrons (so called gas multiplication). One advantage with this embodiment is that each electron avalanche only induces a signal on one anode element or essentially on one detector electrode element. The position resolution in one coordinate is therefore determined by the pitch.

It shall be appreciated that while the FIGS. 5–7 embodiments have been described to have resistive or semiconducting layers on their respective electrode surfaces, they may equally well be provided with any of the other inventive spark discharge-limiting features; e.g. the may be made entirely in any of the materials described above or they may designed as the electrodes illustrated in FIGS. 2–4.

In a particular version of the invention (not illustrated) the electron avalanche amplification device may be dispensed with, and avalanche amplification can be achieved simply by keeping the voltage (i.e. the electrical fields created thereby) between the cathode and the anode/readout arrangements (naturally being provided in accordance with the present invention), during operation, high enough to cause electron avalanche amplification within a single drift/amplification space.

In the embodiments depicted the gas volumes shall be made thin as this results in a fast removal of ions, which leads to low or no accumulation of space charges. This makes operation at high rate possible.

In the embodiments described the inter-electrode distances shall be kept short since this leads to low operating voltages, which results in an even lower energy in possible sparks. This reduces also the risk of damaging the electronics.

The focusing of field lines (which typically is performed in an electron avalanche amplification device) is also favorable for suppressing streamer formations. This leads to a reduced risk for occurrence of sparks.

Further, while some of the above described embodiments of the present invention concentrate on the cathode arrangement it shall nevertheless be readily appreciated that the anode arrangement may alternatively, or additionally, be designed in similar manners.

Generally, the resistances involved at the cathode arrangement should be kept low enough to accept high rate and still high enough to protect the electrodes against sparks.

Although the invention has been described in conjunction with a number of preferred embodiments, it is to be understood that various modifications may still be made without departing from the spirit and scope of the invention, as defined by the appended claims.

For example, although the invention has been described in connection with detectors where the radiation is incident from the side, the invention could be used for detectors where the radiation is incident in any direction. Thus, the invention may particularly be employed in two-dimensional gaseous-based ionizing radiation detectors wherein incident radiation enters the detector through the cathode arrangement.

In such arrangement, however, a severe limitation is a parallax error, which occurs due to divergent radiation beams, extended absorption tracks, and homogenous electric drift fields. Such parallax error problem is solved in our copending Swedish patent application Swedish patent application No. 0003390-2 entitled Parallax-free detection of ionizing radiation and filed on Sep. 22, 2000, which application hereby is incorporated by reference. The solution comprises dividing the cathode and/or anode into segments electrically insulated from each other and to keep the various segments at different selected electric potentials such that an electric field between the electrodes is obtained whose field lines are pointing towards the radiation source of the divergent radiation beam, for drifting charge carriers (e.g. electrons) created during ionization in parallel with the field lines towards the electrodes (the anode in the case of electrons). Thus, it shall be particularly appreciated that such solution may be advantageously combined with any of the embodiments of the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A detector for detection of ionizing radiation comprising:
   a cathode arrangement and an anode arrangement between which a voltage is applicable;
   a space capable of being filled with an ionizable gas and arranged at least partly between said first cathode and said first anode;

a radiation entrance arranged such that ionizing radiation can enter said space between said first cathode and said first anode, for ionizing the ionizable gas; and a readout arrangement; wherein
said voltage is applicable for drifting electrons created during ionization of said ionizable gas towards the anode arrangement; and
said readout arrangement is arranged for detection of the electrons drifted towards the first anode, wherein at least one of the cathode and anode arrangements has at least the surface layer facing the other one of the cathode and anode arrangements made of a material having a resistivity of at least $5\times10^{-8}$ $\Omega$m.

2. The detector as claimed in claim 1 wherein said material has a resistivity between $5\times10^{-8}$ $\Omega$m and $1\times10^{5}$ $\Omega$m.

3. The detector as claimed in claim 1 wherein said material is a semiconducting material.

4. The detector as claimed in claim 3 wherein said semiconducting material comprises a semiconductor material composed of elements selected from the periodic system group IV and/or from the periodic system groups III and V.

5. The detector as claimed in claim 4 wherein said semiconductor material is silicon.

6. The detector as claimed in claim 4 wherein said semiconductor material is doped.

7. The detector as claimed in claim 1 wherein said at least one of the cathode and anode arrangements is made entirely of a semiconducting material.

8. The detector as claimed in claim 1 wherein said material having a resistivity of at least $5\times10^{-8}$ $\Omega$m is electrically connected to a high voltage supply unit, said unit being adapted for application of said voltage between said cathode and anode arrangements.

9. The detector as claimed in claim 1 wherein said surface of said at least one of the cathode and anode arrangements facing the other one of the cathode and anode arrangements is partly covered by a plurality of electrically conductive elements.

10. The detector as claimed in claim 9 wherein said plurality of electrically conductive elements are resistively connected to each other by means of said material having a resistivity of at least $5\times10^{-8}$ $\Omega$m.

11. The detector as claimed in claim 9 wherein said material having a resistivity of at least $5\times10^{-8}$ $\Omega$m is an electric insulator and wherein said plurality of electrically conductive elements are each connected to a high voltage supply unit via a respective resistance arranged adjacent respective electrically conductive element, said unit being adapted for application of said voltage between said cathode and anode arrangements.

12. The detector as claimed in claim 11 wherein each of said plurality of electrically conductive elements and each of said plurality of resistances are provided on said surface of said at least one of the cathode and anode arrangements facing the other one of the cathode and anode arrangements in the form of an stripe having a narrow waist in an end portion thereof, such that the stripe has an elongated portion constituting the electrically conductive element, a narrow waist portion constituting the resistance, and a wider connection portion for connection to said high voltage supply unit.

13. The detector as claimed in claim 12 wherein the material composition of each of said stripes is inhomogeneous such that each elongated portion has a material composition of a second resistivity and said narrow waist portion has a material composition of a third resistivity, said third resistivity being higher than said second resistivity.

14. The detector as claimed in claim 1 wherein the anode arrangement comprises the readout arrangement.

15. The detector as claimed in claim 1 wherein the surface of the other one of the cathode and anode arrangements facing said at least one of the cathode and anode arrangements comprises a plurality of electrically conductive or semiconducting elements.

16. The detector as claimed in claim 8 wherein the surface of the other one of the cathode and anode arrangements facing said at least one of the cathode and anode arrangements comprises a plurality of electrically conductive or semiconducting elements, and wherein said plurality of electrically conductive elements of said at least one of the cathode and anode arrangements extend substantially in a first direction, and said plurality of electrically conductive or semiconducting elements of the other one of the cathode and anode arrangements extend substantially in a second direction, said first and second directions being essentially non-parallel.

17. The detector as claimed in claim 1 wherein said at least one of the cathode and anode arrangements is the cathode arrangement.

18. The detector as claimed in claim 1 wherein said detector comprises an electron avalanche amplification device for avalanche amplifying electrons created during ionization of said ionizable gas; and wherein said readout arrangement is arranged for detection of said avalanche amplified electrons.

19. A device for use in planar beam radiography comprising an X-ray source, means for forming an essentially planar X-ray beam located between said X-ray source and an object to be imaged, and the detector as claimed in claim 1 located and arranged for detection of the planar X-ray beam as transmitted through or reflected off said object.

20. A device for use in planar beam radiography comprising an X-ray source, means for forming an essentially planar X-ray beam located between said X-ray source and an object to be imaged, and a first, a second and a further of the detector as claimed in claim 1 located and arranged for detection of the planar X-ray beam as transmitted through or reflected off said object, which detectors are stacked to form a detector unit, and means for forming an essentially planar X-ray beam for each detector, said means being located between said X-ray source and said object, wherein each detector is located and arranged for detection of the respective planar X-ray beam as transmitted through or reflected off said object.

21. A detector for detection of ionizing radiation, comprising:
first and second electrode arrangements between which a voltage is capable of being applied;
a space arranged between the electrode arrangements and capable of being filled with an ionizable gas;
a radiation entrance arranged such that ionizing radiation is enterable into said space for ionizing the ionizable gas;
a device for electron avalanche amplification of electrons arranged between the first and second electrode arrangements; and
at least one arrangement of readout elements for detection of electron avalanches; wherein
at least one of the first and second electrode arrangements comprises a resistive material having a surface facing the other electrode arrangement.

22. The detector according to claim 21 wherein said at least one of the first and second electrode arrangements includes a substrate made of a resistive material, said substrate being partially covered with a conductive layer.

23. The detector according to claim 22 wherein said at least one of the first and second electrode arrangements includes a substrate made of a resistive material, said substrate being partially covered with a plurality of conductive elements.

24. The detector according to claim 21 wherein said at least one of the first and second electrode arrangements is entirely of said resistive material.

25. The detector according to claim 21 wherein said at least one of the first and second electrode arrangements includes a conductive layer connected to a high voltage supply unit, and a layer of a resistive material arranged adjacent said conductive layer such that said resistive layer is facing the other electrode.

26. The detector according to claim 25 wherein said resistive layer acts as a carrier for the conductive layer.

27. The detector according to claim 21 wherein said other electrode arrangement comprises a resistive material having a surface facing said at least one of the first and second electrode arrangements.

28. The detector according to claim 21 wherein said resistive material is a semiconducting material.

29. The detector according to claim 21 wherein said resistive material is silicon monoxide, conductive glass or diamond.

30. The detector according to claim 21 wherein said device for electron avalanche amplification comprises an electron avalanche cathode and an electron avalanche anode and wherein at least one of the electron avalanche cathode and anode comprises a resistive material having a surface facing the other one of the electron avalanche cathode and anode.

31. The detector according to claim 21 wherein all electrode surfaces of said detector facing said space are covered by said resistive material.

32. The detector according to claim 21 wherein at least one of the first and second electrode arrangements constitutes a drift electrode arrangement for drift of electrons.

33. The detector according to claim 21 wherein at least one of the first and second electrode arrangements constitutes an avalanche electrode arrangement of said device for electron avalanche amplification.

34. The detector according to claim 21 wherein at least one of the first and second electrode arrangements constitutes said arrangement of readout elements for detection of electron avalanches.

35. An apparatus for planar beam radiography comprising:
   an X-ray source;
   means for forming an essentially planar X-ray beam positioned between said X-ray source and an object to be imaged; and
   the detector as claimed in claim 21.

36. An apparatus for planar beam radiography comprising:
   an X-ray source;
   means for forming an essentially planar X-ray beam positioned between said X-ray source and an object to be imaged; and
   a plurality of the detector as claimed in claim 21, wherein the plurality of the detectors are stacked to form a detector unit, means for forming an essentially planar X-ray beam is provided for each detector, said means being positioned between said X-ray source and the object to be imaged, wherein said means for forming an essentially planar X-ray beam and said detector unit are fixed in relation to each other in order to form a unit, which can be used for scanning an object.

37. A detector for detection of ionizing radiation comprising:
   a cathode arrangement and an anode arrangement between which a voltage is applicable;
   a space capable of being filled with an ionizable gas and arranged at least partly between said cathode and anode arrangements;
   a radiation entrance arranged such that ionizing radiation can enter said space between said cathode and anode arrangements, for ionizing the ionizable gas; and
   a read-out arrangement; wherein
      said voltage is applicable for drifting electrons created during ionization of said ionizable gas towards the anode arrangement;
      said read-out arrangement is arranged for detection of the electrons drifted towards the anode arrangement, or correspondingly produced ions; and
      said cathode arrangement has at least a portion of the surface layer facing the anode arrangement made of a material having a resistivity between $1 \times 10^{-3}$ $\Omega$m and $1 \times 10^3$ $\Omega$m.

38. The detector as claimed in claim 37, wherein said surface of said cathode arrangement facing the anode arrangement is partly covered by a plurality of electrically conductive elements.

39. The detector as claimed in claim 38, wherein said plurality of electrically conductive elements are separated from each other.

40. The detector as claimed in ay of claims 38, wherein said plurality of electrically conductive elements are resistively connected to each other by means of said material having a resistivity between $1 \times 10^{-3}$ $\Omega$m and $1 \times 10^3$ $\Omega$m.

41. The detector as claimed in claim 38, wherein said material having a resistivity between $1 \times 10^{-3}$ $\Omega$m and $1 \times 10^3$ $\Omega$m is an electric insulator.

42. The detector as claimed in claim 41, wherein said plurality of electrically conductive elements are connected to each other via respective resistances.

43. The detector as claimed in claim 41, comprising a high voltage supply unit for application of said voltage between said cathode and anode arrangements, wherein said plurality of electrically conductive elements are each connected to said high voltage supply unit via a respective resistance.

44. The detector as claimed in claim 43, wherein each of said plurality of electrically conductive elements and each of said plurality of resistances are provided on said surface of said cathode arrangement facing the anode arrangement in the form of a stripe having a narrow waist in an end portion thereof, such that the stripe has an elongated portion constituting the electrically conductive element, a narrow waist portion constituting the resistance, and a wider connection portion for connection to said high voltage supply unit.

45. The detector as claimed in claim 44, wherein the material composition of each of said stripes is inhomogeneous such that each elongated portion has a material composition of a second resistivity and said narrow waist portion has a material composition of a third resistivity, said third resistivity being higher than said second resistivity.

46. The detector as claimed in claim 38, wherein the surface of the anode arrangement facing said cathode arrangement comprises a plurality of electrically conductive or semiconducting elements.

47. The detector as claimed in claim 46 wherein said plurality of electrically conductive elements of said cathode arrangement extend substantially in a first direction, and said plurality of electrically conductive or semiconducting elements of the anode arrangement extend substantially in a second direction, said first and second directions being essentially non-parallel.

48. The detector as claimed in claim 47, wherein said first and second directions are essentially perpendicular.

49. The detector as claimed in claim 37, comprising a high voltage supply unit for application of said voltage between said cathode and anode arrangements, wherein said high voltage supply unit is electrically connected to said material having a resistivity between $1\times10^{-3}$ $\Omega$m and $1\times10^{3}$ $\Omega$m.

50. The detector as claimed in claim 37, wherein said material has a resistivity between $1\times10^{-2}$ $\Omega$m and 1 $\Omega$m.

51. The detector as claimed in claim 37, wherein said material has a resistivity between $1\times10^{-2}$ $\Omega$m and $1\times10^{-1}$ $\Omega$m.

52. The detector as claimed in claim 37, wherein said material is a semiconducting material.

53. The detector as claimed in claim 52, wherein said semiconducting material comprises a semiconductor material composed of elements selected from the periodic system group IV and/or from the periodic system groups III and V.

54. The detector as claimed in claim 53, wherein said semiconductor material is silicon.

55. The detector as claimed in claim 53, wherein said semiconductor material is doped.

56. The detector as claimed in claim 37, wherein said cathode arrangement is made entirely of a semiconducting material.

57. The detector as claimed in claim 37, wherein the anode arrangement comprises the read-out arrangement.

58. The detector as claimed in claim 37, wherein said detector comprises an electron avalanche amplification device for avalanche amplifying electrons created during ionization of said ionizable gas; and wherein said read-out arrangement is arranged for detection of said avalanche amplified electrons, or correspondingly produced ions.

59. A device for use in planar beam radiography comprising an X-ray source; means for forming an essentially planar X-ray beam located between said X-ray source and an object to be imaged; and the detector as claimed in claim 37 located and arranged for detection of the planar X-ray beam as transmitted through or reflected off said object.

60. A device for use in planar beam radiography comprising an X-ray source; a plurality of the detector as claimed in claim 37, which detectors are stacked to form a detector unit; and means for forming an essentially planar X-ray beam for each detector, said means being located between said X-ray source and said object, wherein each detector is located and arranged for detection of a respective planar X-ray beam as formed and transmitted through or reflected off said object.

* * * * *